US009216156B2

(12) United States Patent
Fleury et al.

(10) Patent No.: US 9,216,156 B2
(45) Date of Patent: Dec. 22, 2015

(54) VIROSOME-LIKE VESICLES COMPRISING GP41-DERIVED ANTIGENS

(75) Inventors: Sylvain Fleury, Bottens (CH); Morgane Bomsel, Paris (FR); Rinaldo Zurbriggen, Schmitten (CH)

(73) Assignees: MYMETICS CORPORATION, New York, NY (US); INSTITUT NATIONAL DE LA SANTE ET DE LA RECHERCHE MEDICALE (INSERM), Paris (FR); PEVION BIOTECH LTD., Bern (CH)

( * ) Notice: Subject to any disclaimer, the term of this patent is extended or adjusted under 35 U.S.C. 154(b) by 1014 days.

(21) Appl. No.: 12/281,256

(22) PCT Filed: Mar. 2, 2007

(86) PCT No.: PCT/IB2007/000502
§ 371 (c)(1),
(2), (4) Date: Jan. 2, 2009

(87) PCT Pub. No.: WO2007/099446
PCT Pub. Date: Sep. 7, 2007

(65) Prior Publication Data
US 2009/0202622 A1 Aug. 13, 2009

(30) Foreign Application Priority Data
Mar. 3, 2006 (WO) .................. PCT/IB2006/000466

(51) Int. Cl.
| A61K 9/127 | (2006.01) |
| C12N 7/00 | (2006.01) |
| A61K 39/12 | (2006.01) |
| A61K 9/00 | (2006.01) |
| A61K 39/21 | (2006.01) |
| C07K 14/005 | (2006.01) |
| A61K 39/00 | (2006.01) |

(52) U.S. Cl.
CPC ............. *A61K 9/1272* (2013.01); *A61K 9/0019* (2013.01); *A61K 9/0043* (2013.01); *A61K 9/127* (2013.01); *A61K 9/1271* (2013.01); *A61K 39/12* (2013.01); *A61K 39/21* (2013.01); *C07K 14/005* (2013.01); *A61K 2039/54* (2013.01); *A61K 2039/545* (2013.01); *A61K 2039/55555* (2013.01); *A61K 2039/6018* (2013.01); *A61K 2039/6075* (2013.01); *C12N 2740/16122* (2013.01); *C12N 2740/16134* (2013.01)

(58) Field of Classification Search
CPC .................. A61K 9/127; A61K 39/21; A61K 2039/55555; A61K 2039/6018; C07K 14/005; C12N 2740/16134
See application file for complete search history.

(56) References Cited

U.S. PATENT DOCUMENTS 6,455,265 B1 9/2002 Serres
7,198,791 B2 * 4/2007 Pluschke et al. ........... 424/185.1

FOREIGN PATENT DOCUMENTS

| EP | 0 538 437 B1 | 8/1999 |
| WO | WO 2004/007800 A1 | 1/2004 |
| WO | WO 2004/045582 A1 | 6/2004 |
| WO | WO 2004/078099 A2 | 9/2004 |
| WO | WO 2005/010033 A1 | 2/2005 |
| WO | WO 2005/049647 A2 | 6/2005 |
| WO | WO 2005/111079 A2 | 11/2005 |

OTHER PUBLICATIONS

Cornet, B., et al., 1990, Virosomes reconstituted from human immunodeficiency virus proteins and lipids, Biochem. Biophys. Res. Commun. 167(1):222-231.*
Matoba, N., et al., 2004, A mucosally targeted subunit vaccine candidate eliciting HIV-1 transcytosis-blocking Abs, Proc. Natl. Acad. Sci. USA 101(37)13584-13589.*
Watkins, B. A., et al., Dec. 1996, Resistance of human immunodeficiency virus type 1 to neutralization by natural antisera occurs through single amino acid substitutions that cause changes in antibody binding at multiple sites, J. Virol. 70(12):8431-8437.*
Huang, W., et al., Jun. 2008, Coreceptor tropism can be influenced by amino acid substitutions in the gp41 transmembrane subunit of human immunodeficiency virus type 1 envelope protein, J. Virol. 82(11):5584-5593.*
Gallo, R. C., et al., Nov. 2005, The end or the beginning of the drive to an HIV-preventive vaccine: a view from over 20 years, The Lancet 366:1894-1898.*
Letvin, N. L., Dec. 2006, Progress and obstacles in the development of an AIDS vaccine, Nature Rev. Immunol. 6:930-939.*
Bron et al., "Preparation, Properties, and Applications of Reconstituted Influenza Virus Envelopes (Virosomes)," *Methods in Enzymology*, 1993, pp. 313-331, vol. 220, Academic Press, Inc.
Stegmann, "Membrane Fusion Mechanisms: The Influenza Hemagglutinin Paradigm and its Implications for Intracellular Fusion," *Traffic* 2000, pp. 598-604, Munksgaard International Publishers.
Monnard et al., "Entrapment of nucleic acids in liposomes," *Biochimica et Biophysica Acta*, 1997, pp. 39-50, Elsevier Science B.V.
Wagner et al., "Enhanced Protein Loading Into Liposomes by the Multiple Crossflow Injection Technique," *Journal of Liposome Research*, vol. 12, No. 3, 2002, pp. 271-283, Marcel Dekker, Inc.
Oberholzer et al., "Enzymatic reactions in liposomes using the detergent-induced liposome loading method," *Biochimica et Biophysica Acta*, 1999, pp. 57-68, Elsevier Science B.V.

(Continued)

*Primary Examiner* — Jeffrey Parkin
(74) *Attorney, Agent, or Firm* — Oliff PLC (57) ABSTRACT

The present invention relates to a virosome-like vesicle comprising at least a gp41-derived antigen or an analogue thereof, said gp41-derived antigen being located to the external surface of and/or encapsulated inside said vesicle and being in a convenient configuration for conferring said virosome-like vesicle with an ability to induce an immune response against a gp41 protein or a human immunodeficiency virus (HIV).

30 Claims, 6 Drawing Sheets

(56) References Cited

OTHER PUBLICATIONS

Skehel et al., "The Polypeptide Composition of Influenza A Viruses," *Virology*, 1971, pp. 396-408, National Institute for Medical Research.

Christodoulides et al., "Immunization with recombinant class 1 outer-membrane protein from Neisseria meningitides: influence of liposomes and adjuvants on antibody avidity, recognition of native protein and the induction of a bactericidal immune response against meningococci," *Microbiology*. vol. 144, 1998, pp. 3027-3037.

Alexander et al., "The Optimization of Helper T Lymphocyte (HTL) Function in Vaccine Development," *Immunologic Research*, 1998, pp. 79-92, Humana Press, Inc.

Lagaye et al., "Cell-to-Cell Contact Results in a Selective Translocation of Maternal Human Immunodeficiency Virus Type I Quasispecies Across a Trophoblastic Barrier by both Transcytosis and Infection," *Journal of Virology*, May 2001, pp. 4780-4791.

Wagner et al., "GMP-Production of Liposomes-A New Industrial Aproach," *Institute of Applied Microbiology*.

Cornet et al., "Virosomes Reconstituted from Human Immunodeficiency Virus Proteins and Lipids." *Biochemical and Biophysical Research Communications*, vol. 167, No. 1, 1990, pp. 222-231.

Matoba et al., "A mucosally targeted subunit vaccine candidate eliciting HIV-1 transcytosis-blocking Abs," *Proceedings of the National Academy of Sciences of the United States of America*, vol. 101, No. 37, 2004, pp. 13584-13589.

Westerfeld et al., "Peptides delivered by immunostimulating reconstituted influenza virosomes," *Journal of Peptide Science*, vol. 11, 2005, pp. 707-712.

Anonymous, "Virosomal Vaccine Platforms," Oct. 2004, Pevion Biotech Ltd, Retrieved from the Internet: URL:http://www.pevion.com/images/content/Pevion_Virosomesheet_vaccines_October04.pdf.

Poltl-Frank et al., "Use of reconstituted influenza virus virosomes as an immunopotentiating delivery system for a peptide-based vaccine," *Clinical and Experimental Immunology*, 1999, pp. 496-503, Blackwell Science, Ltd.

Zolla-Pazner, "Identifying Epitopes of HIV-1 That Induce Protective Antibodies," *Nature Reviews, Immunology*, vol. 4, 2004, pp. 199-210.

Phogat et al., "Hepatitis B Surface Antigen Particles Possessing the HIV-1 gp41 Membrane Proximal Region," $13^{th}$ *Conference on Retroviruses and opportunistic Infections*, 2006, Foundation for Retrovirology and Human Health.

Rosny et al., "Peptides Corresponding to the Heptad Repeat Motifs in the Transmembrane Protein (gp41) of Human Immunodeficiency Virus Type I Elicit Antibodies to Receptor-Activated Conformations of the Envelope Glycoprotein," *Journal of Virology*, vol. 75, No. 18, 2001, pp. 8859-8863, American Society for Microbiology.

Anonymous, "Mymetic's Approach," Retrieved from the internet: URL:http://www.mymetics.com/mymetics_pages/technology_mymetics_02.htm.

* cited by examiner

FIGURE 1

SEQ ID NO 1:
Q ARQLLSGIVQ QQNNLLRAIE AQQHLLQLTV WGIKQLQARI LAVERYLKDQ
QLLGIWGCSG KLICTTAVPW NASWSNKSLE QIWNHTTWME WDREINNYTS
LIHSLIEESQ NQQEKNEQEL LELDKWASLW NWFNITNWLW YIK

SEQ ID NO 2:
SQ TQQEKNEQEL LELDKWASLW NWFDITNWLW YIK

SEQ ID NO 3:
SQTQQEKNEQELLALDSWKNLWNWFSITNWLWYIK

SEQ ID NO 4:
SQTQQEKNEQELLALDSWKNLWNWFSITNWLWYIKLGC

FIGURE 2

SEQUENCE 5 :
QPMALI VLGGVAGLLL FIGLGIFFCV

SEQUENCE LISTING

<160> NUMBER OF SEQ ID NOS: 5

<210> SEQ ID NO 1
<211> LENGTH: 143
<212> TYPE: PRT
<213> ORGANISM: Homo Sapiens

```
<400> SEQUENCE: 1

Gln Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
            20                  25                  30

Gly Ile Lys Gln Leu Gln Ala Arg Ile Leu Ala Val Glu Arg Tyr Leu
        35                  40                  45

Lys Asp Gln Gln Leu Leu Gly Ile Trp Gly Cys Ser Gly Leu Ile Cys
    50                  55                  60

Thr Thr Ala Val Pro Trp Asn Ala Ser Trp Ser Asn Lys Ser Leu Glu
65                  70                  75                  80

Gln Ile Trp Asn His Thr Thr Trp Met Glu Trp Asp Arg Glu Ile Asn
                85                  90                  95

Asn Tyr Thr Ser Leu Ile His Ser Leu Ile Glu Glu Ser Gln Asn Gln
            100                 105                 110

Gln Glu Lys Asn Glu Gln Glu Leu Leu Glu Leu Asp Lys Trp Ala Ser
        115                 120                 125

Leu Trp Asn Trp Phe Asn Ile Thr Asn Trp Leu Trp Tyr Ile Lys
    130                 135                 140

<210> SEQ ID NO 2
<211> LENGTH: 35
<212> TYPE: PRT
<213> ORGANISM: Homo Sapiens

<400> SEQUENCE: 2

Ser Gln Thr Gln Gln Glu Lys Asn Glu Gln Glu Leu Leu Glu Leu Asp
1               5                   10                  15

Lys Trp Ala Ser Leu Trp Asn Trp Phe Asp Ile Thr Asn Trp Leu Trp
            20                  25                  30

Tyr Ile Lys
        35

<210> SEQ ID NO 3
<211> LENGTH: 35
<212> TYPE: PRT
<213> ORGANISM: Homo Sapiens

<400> SEQUENCE: 3

Ser Gln Thr Gln Gln Glu Lys Asn Glu Gln Glu Leu Leu Ala Leu Asp
1               5                   10                  15

Ser Trp Lys Asn Leu Trp Asn Trp Phe Ser Ile Thr Asn Trp Leu Trp
            20                  25                  30

Tyr Ile Lys
        35

<210> SEQ ID NO 4
<211> LENGTH: 38
<212> TYPE: PRT
<213> ORGANISM: Homo Sapiens

<400> SEQUENCE: 4

Ser Gln Thr Gln Gln Glu Lys Asn Glu Gln Glu Leu Leu Ala Leu Asp
1               5                   10                  15

Ser Trp Lys Asn Leu Trp Asn Trp Phe Ser Ile Thr Asn Trp Leu Trp
            20                  25                  30

Tyr Ile Lys Leu Gly Cys
        35
```

```
<210> SEQ ID NO 5
<211> LENGTH: 26
<212> TYPE: PRT
<213> ORGANISM: Homo Sapiens

<400> SEQUENCE: 5

Gln Pro Met Ala Leu Ile Val Leu Gly Gly Val Ala Gly Leu Leu Leu
1               5                   10                  15

Phe Ile Gly Leu Gly Ile Phe Phe Cys Val
            20                  25
```

VIROSOME-LIKE VESICLES COMPRISING GP41-DERIVED ANTIGENS

The present invention relates to a novel virosome-like vesicle suitable for inducing an immune response against a human immunodeficiency virus (HIV), pharmaceutical compositions comprising said virosome-like vesicles, method of treatment and kit for inducing an immune response against a human immunodeficiency virus.

The HIV is a retrovirus that gradually destroys the immune system and ultimately leads to the Acquired Immunodeficiency Syndrome (AIDS).

HIV exists under many different versions like members of a large family.

By sequencing the viral genomes, researchers have been able to map out the family tree of HIV. At the root of the tree, there are three groups called M, N and O, group M being responsible for the current AID.S pandemic.

Group M is split into nine genetic subtypes, also called nine clades (designated A through K, with no E or I). The original definition of clades was based on short genomic sequences, mostly within the HIV envelope protein (Env: gp160).

These nine clades have uneven geographic distribution patterns. Clade C circulates in South Africa, India and parts of China. Clade A and D are common in East Africa and clade B is common in North & South America and Western Europe. According to the statistics, the four clades A, B, C and D account for over 90% of all infection worldwide, and clade C represents the world dominant HIV by itself (>60%).

Until recently, vaccine development was focusing on clade B strains, which dominate the epidemic in industrialized countries but cause only about 12% of infections globally.

Most of the vaccine approaches against HIV-1 have targeted the viral envelope (Env) glycoproteins because they are the major surface antigens expressed on virions and by HIV-1 infected cells. The native HIV-1 envelope glycoprotein is an heterotrimer containing three gp120 proteins non-covalently associated with three gp41 glycoproteins.

The three most potent HIV-1 neutralizing antibodies yet identified, b12, 2G12 and 2F5, have a high affinity for the native trimer.

There is increasing effort to develop recombinant proteins as candidate vaccines that are better antigenic mimics than the native envelope glycoprotein complex such as the gp120/gp41.

However, due to numerous (at least fifteen) molecular homologies between the gp120/gp41 and molecules of the immune system, many potential cross-reactivities events may occur leading to possible harmful autoimmune phenomena.

Various strategies have been described in order to dampen those cross-reactivities for obtaining anti-HIV vaccines with no or less cross reactivities with human proteins as the introduction of mutations and/or deletions in various part of the gp41 proteins as described in U.S. Pat. No. 6,455,265 and WO 2005/010033.

However there is still a need for a vaccine that allows for inducing a versatile immune response against HIV infection, and in particular HIV-type 1 infection.

There is also a need for the development of non-clade B vaccines, such as, for example, clade C strains.

There is also a need for the development of a vaccine with broad inhibitory spectrum allowing for cross-clade inhibition.

There is a need for a vaccine allowing to induce a humoral and/or cellular immune response against HIV infection.

There is a need for a vaccine allowing to induce an immune response against HIV infection at the mucosal surface level and at the blood level.

There is a need for a vaccine suitable for inducing mucosal sIgA antibodies and systemic IgG antibodies capable of interfering with HIV entry across the mucosa and early cell infection under the mucosa.

There is a need for a vaccine suitable for inhibiting or reducing HIV entry across mucosal tissues through various mechanisms such as transcytosis.

It is an object of the invention to satisfy to all those above-mentioned needs.

Therefore, according to one of its first aspect, the instant invention is related to a virosome-like vesicle comprising at least a gp41-derived antigen or an analogue thereof, said gp41-derived antigen being located to the external surface of and/or encapsulated inside said vesicle and being in a convenient configuration for conferring said virosome-like vesicle with an ability to induce an immune response against a gp41 protein of a human immunodeficiency virus (HIV).

In particular, the HIV may be of type 1.

The inventors have surprisingly observed that it was possible to induce an immune response at the mucosal surface level as well as a systemic immune response by immunizing rabbits either intramuscularly or intra-nasally with virosome like vesicles comprising a gp41 derived antigen attached at the external surface.

More particularly, the inventors have observed the presence of specific antibodies anti-gp41 protein (mucosal IgA and IgG) in cervico-vaginal and intestinal secretions from rabbits following intramuscularly or intra-nasally immunization.

Specific IgG anti-HIV antibodies were also identified in the sera of those rabbits.

Additionally, those specific antibodies were able to inhibit transcytosis of HIV in different experiments.

The inventors have also observed that antibodies anti-gp41 (mucosal IgA, and IgG) may be obtained in vaginal secretions and rectal washes of female macaques immunized with a vaccine of the invention administered intramuscularly and/or intranasally.

Those secretions and washes were demonstrated as significantly inhibiting HIV transcytosis of various primary clades (B and C) on a human epithelium model.

Therefore, a HIV vaccine according to the invention exhibits, as a property, an ability of eliciting immune responses (CTL and/or antibodies) in the blood as well as at the primary entry site which are the reproductive-genital tracts and intestine/rectal mucosal tissues.

This property is particularly advantageous, because HIV infection may comprise a viral transcytosis step on mucosal surface that facilitates virus translocation and spreading into the body.

Semen and cervico-vaginal secretions may potentially transmit HIV to the gastrointestinal, anorectal and genitourinary tracts because they contain cell-free HIV particles and numerous HIV-infected mononuclear cells.

It is also believed that the major site of early viral replication in HIV-infected subjects is the intestine and other mucosal sites. This is mainly because the vast majority of susceptible cells (intestinal CD4+ T cells) reside in mucosal tissues and within the first few weeks post-HIV exposure, these cells are destroyed.

Within the meaning of the invention, the expression “virosome-like vesicle” is intended to mean a vesicle comprising at least in part virosomal lipids and fusion proteins or fragments thereof, said fragments having the fusion activity and characteristics of the complete fusion protein, at least in an extent serving for the fusion with a biological membrane of the target cell.

WO 2004/07800 has proposed virosome-like vesicles as vectors for malaria antigens cross-linked to the external surface of said vesicles.

Within the meaning of the invention, the expression "gp41-derived antigen" is intended to refer to any part or fragment, as well as the whole protein, of a gp41 protein naturally occurring in any strain of HIV or comprising any modification (aminoacid mutation or chemical modification) which does not substantially affect its antigenic properties.

The antigenic properties of the virosome-like vesicles of the invention follow from the convenient configuration of the gp41-antigen encapsulated inside and/or located to the surface of said vesicles.

WO 2004/045582 describes the preparation of virosome-like vesicles that may comprise gp41/gp120 protein, but which are not concerned with antigenic properties of this protein but only with its fusogenic property.

According to another of its aspects, the instant invention is directed to a pharmaceutical composition comprising virosome-like vesicles according to the invention.

According to another of its aspects, the instant invention is also related to a use of at least one virosome-like vesicle in accordance with the instant invention for the manufacture of a pharmaceutical composition intending to induce an adaptative immune response and/or an innate immune response directed against a gp41 protein of a human immunodeficiency virus.

According to an embodiment, an object of the invention is to induce an IgG and mucosal IgA. Mucosal IgA may be a mixed between IgA and secretory IgA response.

According to another embodiment, an object of the invention is to inhibit or reduce HIV transcytosis, in particular at musosal level.

Within the meaning of the invention, the expression "adaptative immune response" is intended to refer to an immune response relying upon the activation of the immune system component implying specificity and memory with respect to an antigen or a pathogen.

Such a response may be highly specific toward an antigen or a pathogen and is more effective on second and subsequent encounter, with the antigen or pathogen.

Such adaptative immune response may rely on the activation of lymphocytes, such as T-cells or B-cells.

Within the meaning of the invention, the expression "innate immune response" is intended to refer to a response relying upon non-specific recognition system and does not alter upon subsequent encounter with the antigen or pathogen.

Such system may rely upon immune cells such as, for example, monocytes macrophages or natural killer (NK) cells.

According to another of its aspects, the instant invention is also directed to a method of treatment and/or prophylaxis of a HIV infection comprising at least a step of administration to an individual in need thereof an effective amount of virosome-like vesicles in accordance with the invention.

According to another of its aspects, the instant invention is also directed to a kit for inducing an immune response against a gp41 protein of a human immunodeficiency virus comprising:

at least a first virosome-like vesicle according to the invention comprising at least a first gp41-derived antigen, and
at least a second virosome-like vesicle according to the invention comprising at least a second gp41-derived antigen, said first and second gp41-derived antigens being different one from each other.

Virosome-Like Vesicle

A virosome-like vesicle suitable for the instant invention comprises at least virosomal lipids and exhibits fusion membrane properties.

According to an embodiment, a virosome-like vesicle of the invention may comprise an unilamellar lipid bilayer.

According to an embodiment, a virosome-like vesicle of the invention may be a bi- or a multilamellar vesicle.

According to an embodiment, a virosome-like vesicle may have a diameter generally in the range of 100 to 600 nm, and in particular a diameter from 100 nm to 300 nm, and in particular from 200 nm to 400 nm.

Virosome-like vesicles of the invention may be spherical unilamellar vesicles with a mean diameter with approximately 150 nm.

Virosome-like vesicles comprise incorporated into the lipid bilayer fusion proteins or fragments thereof.

The expression "fusion proteins or fragments thereof" is intended to refer to proteins or fragments thereof capable of inducing and/or promoting a fusion reaction between a virosome-like vesicle membrane and a biological membrane of the target cell.

For example, fusion proteins may be influenza membrane glycoproteins such as hemagglutinin (HA).

According to an embodiment, at least two different fusion proteins or fragments thereof may be used, that may display distinct fusion characteristic.

According to another embodiment, distinct fusion characteristics may be, for example, different sensitivity to temperature, to ion concentration, to acidity, to cell type and to tissue type specificity.

According to an embodiment, a virosome-like vesicle may contain fusion proteins that mediate fusion at two distinct temperatures.

According to another embodiment, different viral hemagglutinin (HA) fusion proteins may be used to construct a virosome-like vesicle.

As an example, HA molecules from both X-31 and PR8/34 virions may be capable of catalyzing two distinct fusion reactions at distinct temperatures.

Fusion proteins with different fusion characteristics may be derived from different influenza strains, as other viruses, such as the vesicular stomatitis virus (VSV) E1 protein, the Seliki forest virus (SFV) E1 protein, or the Sendai virus F protein.

The specific fusion mechanism of the virosome-like vesicles allows targeting of the Major Histocompatibility Complex class I (MHC I) or class II (MHC II).

An antigen located to the external surface of a virosome-like vesicle may be degraded upon the endosomal fusion within the endosome and may be presented to the immune system by MHC class II receptors.

An antigen encapsulated inside a virosome-like vesicle may be delivered to the cytosol during the fusion event and may enter the MHC class I pathway.

Therefore, a virosome-like vesicle may be able to induce a humoral and/or a cellular immune response.

In particular, a virosome-like vesicle may be able to induce IgA, such as secretory IgA, as well as IgG.

Protocols of preparation are well-known by the skilled person in the art. Suitable protocols for the invention are described, for example, in WO 2004/045582 or EP 0 538 437, which are incorporated herein by reference.

According to an embodiment, a virosome-like vesicle according to the invention may be obtained either from a virosome vesicle as such, or from a vesicle resulting from the fusion of a virosome vesicle with a liposome vesicle.

Preparation of Virosome Vesicles May be Made by any known Method of the skilled person in the art such as described by Bron et al., Methods Enzymol. 220: 313-331, 30 1993, incorporated herein by reference.

Virosome vesicles, for example, may be reconstituted from original viral membrane lipids and spike glycoproteins after solubilization of, for example, intact influenza virus with octaethyleneglycol monododecyl ether, sedimentation of the nucleocapsid (the viral glycoproteins and lipids will remain in the supernatant), and removal of the detergent in the supernatant with a hydrophobic resin (Big-Beads SM2) (Stegmann et al., Traffic 1: 598-604, 1987).

Preparation of Virosome Vesicles Containing has from Different Strains of viruses, may be performed with, equal amounts of proteins of those viruses solubilized with the non-ionic detergent octaethyleneglycol monododecyl ether.

After removal of the detergent with Bio-Beads SM2, virosome-like vesicles containing different types of fusion proteins may be formed.

According to one embodiment, a virosome-like vesicle according to the invention may be obtained from a fusion of a virosome vesicle with a liposome vesicle.

Therefore, according to one embodiment, a virosome-like vesicle of the invention may comprise virosomal and liposomal lipids.

According to one embodiment, a virosome-like vesicle of the invention may comprise a lipid bilayer comprising lipids chosen from cationic lipids, synthetic lipids, glycolipids, phospholipids, glycerophospholipids, glycosphingolipids like galactosylceramid, sphingolipids, cholesterol and derivatives thereof.

Such lipids may be used to better mimic the viral membrane and raft microdomain in order to favour optimal gp41 oligomers such as di-, tri- or tetramers.

According to another embodiment, virosome-like vesicles according to the invention may comprise lipids favouring the folding of a gp41-derived antigen in order to more effectively mimic the natural folding of said antigen.

Phospholipids may comprise in particular phosphatidylcholine, sphingomyelin, phosphatidylethanolamine, phosphatidylserine, phosphatidylglycerol, phosphatidic acid, cardiolipin and phosphatidylinositol with varying fatty acyl compositions.

Cationic lipids may be chosen from DOTMA (N-[1-(2,3-dioleylaxy)propyl]-N,N,N-trimethylammonium chloride), DOTAP (N-[1-(2,3-dioleoyloxy)propyl]-N,N,N-trimethylammonium chloride, DODAC (N,N-dioleyl-N,N,-dimethylammonium chloride), DDAB (didodecyldimethylammonium bromide) and stearylamine or other aliphatic amines and the like.

The lipids used in the invention may be formulated as small unilamellar liposomes in a mixture with DOPE (dioleoylphosphatidyl ethanolamine) that is widely used as helper lipid to facilitate disruption of the endosomal membrane.

According to an embodiment, the liposomal lipids of the liposomes may comprise POPC/DDAB.

According to another embodiment, co-emulsifying agent may be also used in order to improve the rigidity and/or the sealing of the vesicles.

As example of co-emulsifying agent, mention may be made of cholesterol and derivatives, as for example cholesterol ester charged or neutral as cholesterol sulphate; derivative with sterol backbone, as for example derivative from vegetal origin as phytosterol (sitosterol, sigmasterol, . . . ); ceramides; and mixtures thereof.

A gp41-derived antigen may be incorporated inside liposomes vesicles before fusion with virosomes.

Encapsulation of at least one antigen and/or adjuvant as indicated below into liposomes may be performed by any method known in the art, including the procedures described in Monnard et al., Biochim. Biophys.; Acta 1329: 39-50; 1997, in Wagner et al., J. Liposome Res., 12(3) 271-283, 2002, or in Oberholzer et al., Biochim. Biophys. Acta 1416: 57-68i 1999, among many other well-known methods.

In a particular embodiment, high liposomal encapsulation efficiencies may be achieved by the freeze/thaw technique used to prepare pure lipid vesicles.

According to one embodiment of the invention, the reaction products of a virosome-liposome fusion reaction may be subjected to a nucleopore extrusion step in order to reduce its size.

As for example extrusion through 200 nm pores may yield vesicles of approximately half of the original size.

Most particles may range from 100 to 300 nm.

After resizing, the products of the liposome-virosome fusion may be virosome-like vesicles that may comprise a gp41-derived antigen in their internal cavity and may be still capable of undergoing a second fusion step, under different conditions, with biological membranes in order to deliver said antigen.

A gp41-derived antigen may be located to the external surface of and/or encapsulated inside a vesicle of the invention as described below.

According to one embodiment, a virosome-like vesicle of the invention may further comprise a targeting moiety that target said vesicle to a specific cell or tissue.

A suitable targeting moiety may be chosen from a cell-surface receptor, a chemokine, a cytokine, a growth-factor, an antibody or an antibody fragment, a peptide sequence with specificity or specific charge complementary to an adhesion molecule such as an integrin.

A targeting moiety may be incorporated into, or attached to the lipid bilayer of said vesicle, by any known techniques of the skilled person in the art.

According to another embodiment, a virosome-like vesicle in accordance with the invention may further comprise an additional antigen.

According to one embodiment, a virosome-like vesicle in accordance with the invention may further comprise from one to ten additional antigen(s), and in particular from 2 to 4 additional antigen(s).

Additional antigens may be chosen from HIV-derived peptides, and in particular peptides derived from structural proteins as encoded by env (gp120, gp41), gag (p9, p17, p24) and pol (p66, p32) genes and from regulatory proteins as encoded by nef, rev or tat genes, and mixtures thereof.

GP41-Derived Antigen

A gp41-derived antigen suitable for the instant invention may be any part of the gp41 protein, as well as the gp41 protein in its whole, and analogues thereof.

Within the meaning of the invention, the expression "analogue thereof" with respect to a gp41-derived antigen intends to refer to a peptide having substantial (at least 85%, in particular at least 90% and more particularly at least 95%) amino acid sequence identity or homology (i.e. aminoacid residue replaced with an aminoacid residue of the same family, of similar polarity or charge, for example) with the aminoacid sequence of said gp41-derived antigen, and which has similar or conserved biological properties, in particular with respect to binding antigen portion of immunoglobulin directed to the gp41 protein.

According to an embodiment, a gp41-derived antigen suitable for the invention may be devoid of fusogenic property with respect to cell membrane.

According to one embodiment, a gp41-derived peptide located to the external surface of virosome-like vesicle of the invention may be:
- covalently linked with a lipid of said virosome-like vesicle, or
- intercalated into a lipid bilayer of said virosome-like vesicle by a peptide transmembrane domain distinct of a wild-type peptide transmembrane domain of a wild-type gp41 protein.

Accordingly, a covalently linked gp41-derived antigen may comprise any modification required to located said gp41-derived antigen to the external surface of a virosome-like vesicle according to the invention.

Modifications of a gp41-antigen suitable for the invention and methods for cross-linking said modified gp41-antigen to the external surface of a virosome-like vesicle may be as those described in WO 2004/078099.

According to one embodiment, a gp41-derived antigen may be covalently linked to the external surface of a virosome-like vesicle by crosslinking with a lipid or a phospholipid.

According to another embodiment, a gp41-derived antigen may be covalently linked to the external surface of a virosome-like vesicle by cross-linking with a carbohydrate.

According to an embodiment, a covalently linked gp41-derived antigen may comprise at least one N- or C-terminally positioned cross-linking residue.

For example, cross-linking residue mat be chosen from cysteine (Cys) or lysine (Lys).

According to another embodiment a covalently linked gp41-derived antigen may further comprise at least one spacer residue between said N- or C-terminally positioned cross-linking residues and a corresponding N- or C-terminal gp41-derived antigen extremity.

A suitable spacer residue may be chosen, for example, from Gly (glycine), 'Ala' (alanine), Ser (serine), Asp (aspartate), Lys (lysine), Gln (glutamine), His (histidine), Ile (isoleucine) and Leu (leucine) residues.

From 2 to 12, in particular from 3 to 10, and more particularly from 4 to 8, spacer residues may be linked to form spacer sequences.

Suitable spacer sequences may be chosen, for example, from Gly-Gly or Lys-Gly.

Crosslinking of a gp41-derived antigen to the surface of a virosome-like vesicle may be, for example, performed by the use of amphiphilic PEG derivatives, a phosphatidylethanolamine (PE), a phosphatidylcholine (PC), a phosphatidylserine, a cholesterol, or a mixture thereof, readily incorporated into lipids bilayer. Cross-linking of a gp41-derived antigen to a lipid of a virosome-like vesicle of the invention may be performed by any method known to those skilled in the art.

The cross-linking may be operated in a lipid solution and the lipid-peptide conjugate may be subsequently incorporated into a virosome-like vesicle.

According to an embodiment of the invention, a gp41-derived antigen may be linked to a lipid of a vesicle of the invention, for example, by a bifunctional succinate linker, in particular a γ-maleinidobutyric acid N-hydroxysuccinimide ester or a N-γ-maleimidobutyryloxy-succinimide-ester.

According to an embodiment, a gp41-derived antigen, and more particularly an intercalated gp41-derived antigen, may be devoid of its peptide transmembrane domain.

A suitable intercalated gp41-derived antigen may have its peptide transmembrane domain replaced with a distinct peptide transmembrane domain.

Such modified gp41-derived antigen may be a chimeric protein.

Within the meaning of the invention, the expression "chimeric protein" refers to a protein that may contain one or more region from a protein and one or more region from one or more other, distinct, proteins.

For the purpose of the invention, any transmembrane domain of any protein may be suitable to intercalate a gp41-derived antigen into the lipid bilayer of a virosome-like vesicle of the invention.

According to one embodiment, one may use transmembrane domains that may favour oligomerization (as to obtain dimers, trimers or tetramers) such as transmembrane of growth factors receptors or envelope proteins from viruses.

As example of transmembrane domain that may convene to the instant invention, mention may be made of transmembrane domain obtained from cell surface receptor like CD4 receptor (for example as set forth as SEQ. ID. NO. 5), cytokine receptor, as for example IL-1 receptor, EGF receptor, VEGF receptor, any G-protein coupled receptors, any tyrosine kinase receptors, viral transmembrane domain derived from envelop proteins of viruses such as viruses of the rhabdovirus family or the poxvirus family. Suitable virus protein for the invention may be for example the vesicular stomatis virus protein G (VSV-G).

Such transmembrane domains are well known in the art, and may be easily identified by a skilled person in the art.

A chimeric protein suitable for the instant invention may be obtained by any genetic engineering techniques known by the skilled person in the art, such as described in "Molecular Cloning—A Laboratory Manual" ($2^{ND}$ Ed.) Sanbrook et al., 1990, Coldspring Harbor Laboratory, Coldspring Harbor Press N.Y. (Sanbrook).

According to another embodiment, a gp41-derived antigen may be provided to the external surface of a virosome-like vesicle under a mono-, di-, tri- and more particularly under a tetrameric form, and mixtures thereof.

Therefore, the amount of gp41-derived antigen to be used to prepare a virosome-like vesicle in accordance with the invention may be adjusted by any routine protocol known by the skilled person in the art to obtain the desired mono- or multimeric form.

According to an embodiment, a gp41-derived antigen may be located to the external surface by its N- or C-terminal extremity.

According to one embodiment, a gp41-derived antigen may be located to the external surface by its C-terminal extremity.

According to one embodiment, a gp41-derived antigen may be located to the external surface by its N-terminal extremity.

According to an embodiment, a gp41-derived antigen may be encapsulated inside a virosome-like vesicle of the invention.

A gp41-derived antigen may be encapsulated by a virosome, by methods well known in the art.

For example, a solution of purified influenza A/Singapore hemagglutinin obtained as described previously by J. J. Skehe and G. C. Schild (The polypeptide composition of influenza A viruses. Virology 44 (1971) 396-408) may be prepared by dissolution of a pellet of hemagglutinin centrifuged into a solution of PBS-OEG (phosphatidylcholine (PC), phosphatidylethanolamine (PE) dissolved in PBS containing octanethyleneglycolmonodecylether (OEG).

Gp41-derived antigens and phospholipids may be added to the hemagglutinin-solution, mixed, sonicated then centrifuged. Virosomes may be then formed, as previously described, by detergent removal for example using BioRad SM Bio-Beads.

According to another example, a gp41-derived antigen may be encapsulated into liposomes using methods such as previously described or as described in Christodoulides et al., Microbiology 144:3027-3037 (1998), before the fusion of said liposomes vesicles with virosomes vesicles.

According to another embodiment, when encapsulated into a virosome-like vesicle of the invention, a gp41-derived antigen may also be provided under a mono- or multimeric form as previously indicated.

According to an embodiment, a gp41-derived antigen that may be used in the instant invention may be chosen from any HIV clades.

Suitable HIV clades for the invention may be for example HIV from A, B, C or D clades.

More particularly, a gp41-derived antigen may be from HIV type C clades.

A suitable gp41-derived antigen may comprise in part any conservative amino-acid substitution (and/or insertion and/or deletion) and/or chemical modification (such as cyclization) with respect to the naturally occurring of the gp41-derived antigen, the implementation of which may rely upon the routine skill of a skilled person in the art.

According to one embodiment, a gp41-derived antigen that may convene to implement the instant invention may be a peptide of amino acids sequence represented in all or part by a sequence set forth as SEQ. ID. NO. 1, obtained from the HIV-1 strain HxB2, or an analogue thereof.

In one embodiment, a gp41-derived antigen may be a gp41 engineered loop proteins derived from the wild-type amino acids sequences of the gp41 glycoproteins of HIV.

As example of gp41-derived antigens that may be useful to carry out the instant invention mention may be made of gp41-derived antigens obtained by introducing in the immunodominant regions some mutations (deletion, substitution and/or insertion) in order to reduce the homology with the human interleukine-2 (IL-2) as to avoid or reduce the risk of triggering an autoimmune reaction. Such gp41-derived antigens are in particular described in WO 2005/010033, which is incorporated herein by reference.

In the present application, "mutation" refers to any modification of a region (optionally reduced to a single amino acid residue) of a polypeptide, by physical means, chemical means (covalent or non-covalent modification) and/or biological means (mutations by substitution, deletion and/or insertion of one or more amino acids), leading to the modification of the functional potentials of the constituent amino acid(s) of said region, termed "mutated region". By way of example, it is possible to carry out mutations leading to the modification of an aminoacid of L series into D series, the abolition, acquisition and/or modulation of the properties of disulfide bridges, hydrogen bonds, electrostatic interactions and/or hydrophobic interactions, the modification of the capacity of a protein to form a heterocomplex, or alternatively, in the case of an oligomeric protein, the modification of the state of oligomerization or of the stability of the oligomer.

The modification of the immunodominant regions may result in the introduction in, or replacement of part of, the loop with a hydrophilic and non or weakly immunogenic, flexible linker and optionally with the introduction of mutation(s).

Gp41-derived antigen may include furthermore at least one mutation in its immunodominant region, which give in vitro a cross-reaction, of the B type and/or the T type, with a host protein and in particular with IL-2.

Some of the mutations decisive to impact this change in the antigenicity are disclosed in U.S. Pat. No. 6,455,265 and WO 2005/010033 which teachings are incorporated by reference herein in their entirety.

According to an embodiment, a gp41-derived antigen suitable for the instant invention may be a peptide called P1 and may be a peptide of amino acid sequence represented in all or part by a sequence chosen from SEQ. ID. NO. 2, SEQ. ID. NO. 3 or an analogue thereof.

The peptide P1 corresponds to an amino acid sequence present in the HIV envelope protein ectodomain gp41 that is located at the surface of the viral particles before the viruses interact with target cells. As example, in the HIV-1 HxB2 strain, this sequence is comprised from amino acid 649 to amino acid 683 of the wild-type gp41 protein.

A gp41-derived antigen useful for the invention may also include modifications such as truncation of a part of the amino acids sequence at the N- or C-terminal extremities or addition of peptide sequence to produce chimeric protein, as described in WO 2005/010033, or as previously described.

As an example of a gp41-derived antigen suitable for the invention, the peptide P1 sequence comprising an addition of a Leu-Gly-Cys spacer at the C-terminal position may be envisioned, as, for example, set forth as SEQ. ID. NO. 4.

Adjuvants

According to an embodiment, the immunostimulatory effect of virosome-like vesicles of the invention may be further increased by associating those virosome-like vesicles with at least one adjuvant.

Said adjuvant may be encapsulated inside and/or incorporated in the lipid bilayer of, and/or freely combined with said vesicle.

According to one embodiment, a virosome-like vesicle may additionally comprise at least one adjuvant enhancing and/or mediating an immune response chosen from an innate immune response and/or an adaptative immune response.

An adaptative immune response may be chosen from a $T_{H1}$ and/or $T_{H2}$ immune response.

Usable adjuvants may enhance the immunological response by activating antigen presenting cells (APC), macrophages and/or stimulating specific sets of lymphocytes.

An adjuvant that may convene to the instant invention may be any ligand suitable for the activation of a pathogen recognition receptor (PRR) expressed in and on dentritic cells (DCs) or other antigen presenting cells.

Ligands activating the Toll-like receptors (TLRs) may also convene for the purpose of the invention. Those receptors are member of the PRR family and are widely expressed on a variety of innate immune cells, including DCs, macrophages, mast cells and neutrophils.

As example of ligands activating TLR, mention may be made, with respect of TLR4 of LPS from *E. coli*, taxol, RSV fusion protein, and host heat shock proteins 60 and 70, with respect of TLR2 of peptidoglycan of *Staphylococcus aureus*, lipoproteins from *M. tuberculosis*, and *Sacharomyces cerevisiae* zymosan, and highly purified *P. gingivalis* LPS, with respect of TLR3 of dsRNA, with respect of TLR5 of flagellin, with respect TLR7 of synthetic compounds imidazoquinolines and with respect of TLR9 of certain types of CpG-rich DNA.

Other useful adjuvants for the invention may be T helper epitopes.

A T helper epitope is a peptide usually derived from exogenous proteins that have undergone proteolytic degradation and processing within the endocytic pathway of antigen presenting cells (APCs). In those cells the Major Histocompatibility Complex of class II (MHC II) transported to endosomes of the endocytic pathway associate with those peptides. This complex transported to the surface of the APCs may interact with a specific T cell receptor of T lymphocytes $CD4^+$ leading to their activation.

According to the helper epitope, the T cell response may be of $T_{H1}$ and/or $T_{H2}$ type.

$T_{H1}$ epitopes favouring a CTL response and $T_{H2}$ epitopes favouring a humoral response are known in the art.

As example of $T_{H1}$-oriented response epitope mention may be made of the mellitin derived peptides identified in WO 2005/049647.

As example of other $T_{H2}$-oriented response epitope one may mention pan DR helper T cell epitope (PADRE). This epitope is engineered to bind most common HLA-DR molecules with high affinity and to act as a powerful immunogen. The PADRE HTL epitope has been shown to augment the potency of vaccines designed to stimulate a cellular immune response (Alexander J. et al, Immunol Res. 1998; 18(2):79-92).

According to an embodiment, an adjuvant that may be used with the virosome-like vesicles of the present invention may be chosen from aluminum salts, aluminum phosphate gels, mycobacteria such as BCG, *M. Vaccae*, or *corynebacterium parvum*, peptides, keyhole limpet hemocyanin, muramyl dipeptides and tripeptide derivatives, monophosphoryl Lipid A, interleukin-2 (IL-2), IL-12, GM-CSF, ligands from the chemokine family, such as RANTES (Regulated upon Activation Normal T cell Expressed and Secreted), a lipoprotein of Gram$^+$ bacteria, a yeast cell wall component, a double-stranded RNA, a lipopolysaccharide of Gram$^-$ bacteria, flagellin, a U-rich single-stranded viral RNA, a CpG containing DNA, a Suppressor 6f Cytokine Signalling small interfering RNA (SOCS siRNA), mellitin derived peptides, a pan DR epitope (PADRE) and mixtures thereof.

Pharmaceutical Preparations

According to an embodiment, virosome-like vesicles according to the invention may be used for the preparation of a pharmaceutical composition intended to induce an adaptative immune response and/or an innate immune response directed against a gp41 protein of a human immunodeficiency virus.

Such pharmaceutical composition may comprise a solution of virosome-like vesicles suspended in a pharmaceutical acceptable carrier, for example an aqueous carrier.

A variety of aqueous carriers may be used e.g., water, buffered water, 0.4% saline, 0.3% glycine, hyaluronic acid and the like. A pharmaceutical composition may be sterilized by conventional, well-known sterilization techniques, or may be sterile filtered.

The resulting aqueous solutions may be packaged for use as is, or lyophilized, the lyophilized preparation being combined with a sterile solution prior to administration.

A pharmaceutical composition may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, among many others.

Such preparations may routinely contain pharmaceutically acceptable concentrations of salt, buffering agents, antioxidants, preservatives, compatible carriers, adjuvants as previously described and optionally other therapeutic agents.

Virosome-like vesicles of the invention, and in particular pharmaceutical compositions comprising thereof may be administered by injection or by a mucosal route, or a combination thereof.

Injection route may be, for example, intraperitoneal, intradermal, subcutaneous intravascular or intramuscular route.

Any mucosal route may be used, such as genito-urinary route as for example vaginal route, gastrointestinal route, anorectal route, respiratory route, upper mucosal tissue, mouth-nasal route and mixtures thereof.

In one embodiment, a pharmaceutical composition of the invention may be provided as oral dosage forms, such as tablets, capsules (each including timed release and sustained release formulations), pills, powders, granules, elixirs, tinctures, solutions, suspensions, syrups and emulsions.

All of these forms are well known to those of ordinary skill in the pharmaceutical arts.

In one embodiment, a virosome-like vesicle may be used for the preparation of a pharmaceutical composition to be administered in the form of a vaccine. Any immunization protocols standard in the art may be used.

According to one embodiment, a pharmaceutical composition of the invention may comprise vesicles comprising a gp41-derived antigen located to the external surface of said vesicles and vesicles comprising a gp41-derived antigen encapsulated inside said vesicles, as a combined preparation for simultaneous, separate or sequential use in immunotherapy.

According to another embodiment, a pharmaceutical composition of the invention may comprise further additional virosome-like vesicles comprising an antigen distinct from said gp41-derived antigen as a combined preparation for simultaneous, separate or sequential use in immunotherapy.

Said distinct antigen may be as previously described.

A pharmaceutical composition of the invention may comprise virosome-like vesicles of the invention in an effective amount.

An effective amount is that amount of virosome-like vesicles that alone, or together with further doses may stimulate the desired response. An effective amount may depend upon a variety of factors, such as the route for administration, whether the administration is in single or multiple doses, and individual patient parameters including age, physical condition, size, weight, and the stage of the disease. These factors are well known to those of ordinary skill in the art and can be addressed with no more than routine experimentation.

Therefore, according to an embodiment, a pharmaceutical composition may comprise virosome-like vesicles of the invention alone or a combination with at least one adjuvant, as previously described.

According to another aspect, the instant invention is also directed to a method of treatment and/or prophylaxis of a HIV infection comprising at least a step of administration to an individual in need thereof an effective amount of virosome-like vesicles according to the instant invention.

According to one embodiment, the virosome-like vesicles in accordance with the invention may be administered by injection or a mucosal route, or a combination thereof as previously indicated.

According to another embodiment, the virosome-like vesicles that may be used in accordance with the instant invention may be virosome-like vesicles comprising a gp41-derived antigen located to the external surface and virosome-like vesicles comprising a gp41-derived antigen encapsulated inside said vesicles as a combined preparation for simultaneous, separate or sequential use in immunotherapy.

According to another embodiment the virosome-like vesicle that may be used in the method in accordance with the invention may be administered in a combination with an additional antigen distinct from said gp41-derived antigen.

As example of additional antigen that may convene to the instant invention, mention may be made of the previously cited distinct antigens.

According to another if its aspects, the instant invention also relates to a kit for inducing an immune response against a gp41 protein of a human immunodeficiency virus comprising:
  at least a first virosome-like vesicle according to the invention, comprising at least a first gp41-derived antigen, and
  at least a second virosome-like vesicle of the invention comprising at least a second gp41-derived antigen,
said first and second gp41-derived antigens being different from one each other.

According to one embodiment, a first gp41-derived antigen may be a peptide of amino sequence represented in all or part by a sequence chosen from SEQ. ID. NO. 2, SEQ. ID. NO. 3, or an analogue thereof.

According to another embodiment, a second gp41-derived antigen may be a peptide of amino acid sequence represented in all or part by a sequence set forth as SEQ. ID. NO. 1, or an analogue thereof.

The instant invention will be further understood with the following examples which are presented for illustrating purposes and should not be interpreted as limiting the scope of the instant invention.

The various aspects of the instant invention will be further illustrated by the following examples, which should not in any case be constructed as limiting the scope of the instant invention.

EXAMPLES

Example 1

Preparation of Virosome-Like Vesicles Comprising a gp-41 Derived Antigen Located to the External Surface Virosome-like vesicles were prepared as described in WO 2004/045582.

Briefly, 32 mg egg phosphatidylcholine (PC) and 8 mg of phosphatidylethanolamine (PE) were dissolved in 2 ml of PBS containing 100 mM of octaethyleneglycolmonodecylether (OEG) (PBS/OEG).

Influenza A/Singapore hemagglutinine (HA) was purified as described (Skehel and Schild, Virology 44:396-408, 1971) in phosphate buffered saline (PBS) 4 mg hemagglutinine (HA) was centrifuged at 100,000×g for 30 min and the pellet was dissolved in 1,33 ml of PBS containing 100 mM of OEG.

A modified gp41-derived antigen (P1) with a spacer Leu-Gly-Cys at the C-terminal position (SEQ. ID. NO. 4) was conjugated through a succinate linker at N-terminus to a regioisomer of phosphatidylethanolamine (PE) as follows.

Phosphatidylethanolamine (PE) was dissolved in methanol and 0.1% (v/v) triethylamine was added. The solution was then mixed with the heterobifunctional cross-linker N-γ-maleimidobutyryloxy-succinimide-ester (GMBS), (Pierce Chemical Company, Rockford, Ill.) (ratio PE: GMBS=5:1) which was previously dissolved in dimethylsulfoxide (DMSO) (20 µl). After incubation during 30 minutes at room temperature, the solvents were evaporated for 1 h under vacuum in a speedvac centrifuge. The GMBS-PE was then dissolved in 1 ml of PBS containing 100 me octaethyleneglycol (OEG) (Fluke Chemicals, Switzerland), (PBS-OEG) and the modified gp41-derived antigen P1 (SEQ. ID. NO. 4) was added (ration PE-GMBS:peptide=5:1). In this step, the phosphatidylethanolamine-GMBS react with a free C-terminal cystein of the modified peptide P1. After in incubation time of 30 minutes, free cystein was added, in order to inactivate free GMBS (ratio Cystein:GMBS=10:1).

Peptide P1-phosphatidylethanolamine conjugates (4 mg), phosphatidylcholine (32 mg; Lipoid, Ludwigshafen, Germany) and phosphatidyl-ethanolamine (6 mg) were dissolved in a total volume of 2.66 ml of PBS-OEG. The phospholipids and the hemagglutinine solutions were mixed and sonicated for 1 min.

This solution was centrifuged for 1 hour at 100 000 g and the supernatant was sterilized by filtration. Virosomes were formed by detergent removal (SM BioBeads, BioRad, Glattbrugg, Switzerland).

Example 2

Immunization of Rabbits with a Vaccine Composition Comprising Virosome-Like Vesicle with gp-41 Derived Antigen Peptide P1 Located at the External Surface Three groups of New-Zealand white female rabbits were prepared to receive virosome-like vesicles manufactured as set forth in example 1.

The virosome-like vesicle were either without any adjuvant intramuscularly administered (rabbits 36 and 37), or intra-nasally administered with hRANTES (rabbits 61 and 63), or intra-nasally administered with Heat labile toxin (HLT) (rabbits 64 and 65).

The following regimen of administration was applied.

Four weeks before the first administration of preparations, rabbits received intramuscular injections of inactivated influenza A (100 µl of inactivated influenza A, 0.01 mg/ml).

Thereafter, rabbits received administration of virosome-like vesicles (20 µg, 100 µl) at week 0, 4 and 12, and received an intramuscular boost (10 µg) at week 16 and 22.

Animals were sacrificed at week 28 and various samples were harvested for studying antibodies response-functions.

Pre-immune samples (taken before week 0) were used as controls.

Blood and vaginal secretions samples were taken at week 14, 18, 23 and 28.

HLT virosome-like vesicles vaccinated rabbits were used as control with respect to hRANTES virosome-like vesicles vaccinated rabbits.

Level of total antibodies, IgG and IgA were measured according to the following ELISA protocol.

Peptide P1 (100 ng/100 µl/wells, SEQ. ID. NO. 3) in a bicarbonate buffer 50 mM, pH 9.6 was used to coat Nunc plates over night at 4° C.

Plates were saturated with BSA 3% or milk 5% for 2 hours/37° C., then washed with PBS-Tween 0.5% buffer.

Samples of sera diluted 1/1000 with BSA 3% or cervico-vaginal secretion diluted 1/50 with BSA 3% were incubated for 2 hours at 37° C.

Plates were thereafter rinsed with PBS-Tween 0.5% buffer, and incubated with primary antibodies.

For detection of total antibodies, an anti-rabbit total Ig goat antibody labelled with horseradish peroxydase (HRP) (1/4000) was used.

For detection of rabbit IgA, an anti-rabbit IgG goat antibody (Vector, France) (1/20 000) was used followed with an incubation with streptavidine-HRP (Immunotech) diluted 1/50 000.

For the detection of IgG rabbit antibody, an anti-rabbit IgA goat antibody (Sigma) (1/20 000) was used followed with an incubation with an anti-goat antibody biotin-labelled (Vector) (1/1000), and revealed with streptavidine-HRP (1/50 000).

A 2F5-IgG monoclonal antibody was used as positive control, followed with an incubation with an anti-human IgA biotin-labelled goat Fab'2, (1/5000) (Caltag) and revealed with streptavidine-HRP (1/50 000).

A 2F5-IgA monoclonal antibody was used as positive control, followed with an anti-human IgG goat Fab'2 (1/20 000) and revealed with streptavidine-HRP (1/50 000).

The antibodies were incubated for 1 hour at 37° C.

Colorimetric reaction was triggered by addition of the substrate TMB, and stopped by addition of $H_2PO_4$ 1M.

The optical density (OD) was read at 450 nm.

Figure 1:
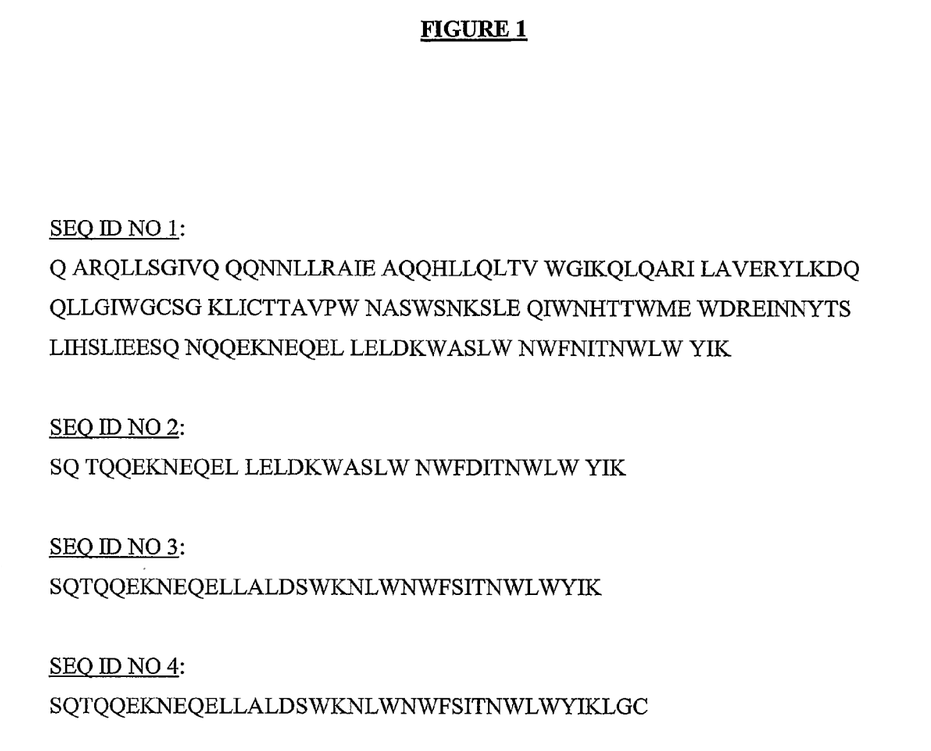
FIG. 1: illustrates gp41-derived antigen sequences form HxB2 clade B virus (SEQ. ID. NO. 1, SEQ. ID. NO. 3, SEQ. ID. NO. 4) and from HIV clade C (SEQ. ID. NO. 2).
Figure 2:
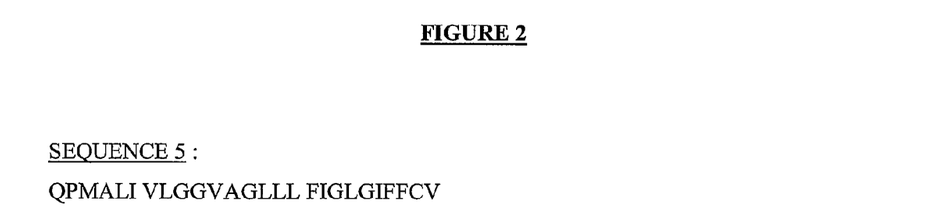
FIG. 2: illustrates a $CD4^+$ molecule transmembrane domain sequence (SEQ. ID. NO. 5).
Figure 3:
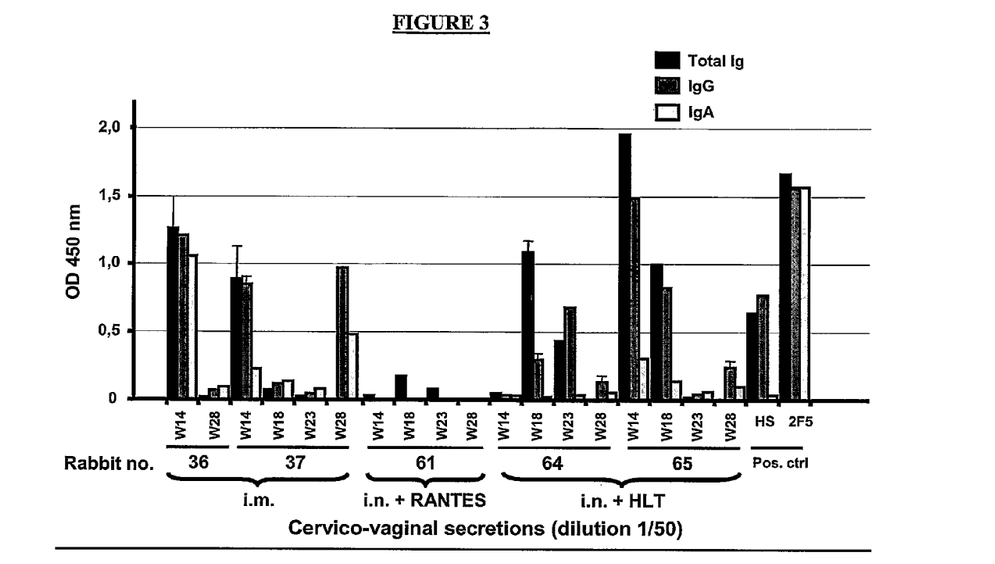
FIG. 3: illustrates dosage of total antibodies, IgG and sIgA in cervico-vaginal secretions from rabbits immunized with virosome-like vesicles-P1 of example 1, without adjuvant (36 & 37, intramuscular route), with hRANTES (61, intra-nasal route) or with heat labile toxin (64 & 65, intra-nasal route) at week 0, 14, 18, 23 and 28.
Figure 4:
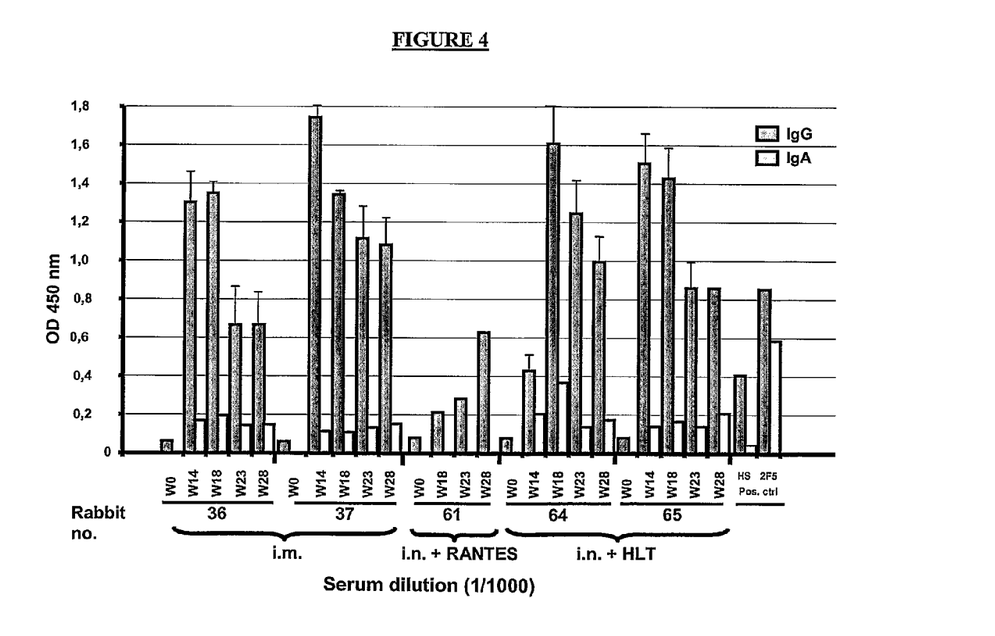
FIG. 4: illustrates dosage of total antibodies, IgG and IgA in sera from rabbits immunized with virosome-like vesicles-P1 of example 1, without adjuvant (36 & 37, intra-muscular route), with hRANTES (61, intra-nasal route) or with heat labile toxin (64 & 65, intra-nasal route) at week 0, 14, 18, 23 and 28.

The obtained results are illustrated on FIG. 3 (cervico-vaginal secretion) and FIG. 4 (sera).

Presence of antibodies was observed in cervico-vaginal secretion and sera from immunized rabbits with a peak at week 14 or 18 according to the immunization conditions.

Example 3

Inhibition of HIV Transcytosis with Cervico-Vaginal Secretion Obtained from Immunized Rabbits from Example 2

HIV-1 transcytosis across epithelial cells and neutralisation of transcytosis by antibodies were performed on epithelial cell line HT-29 grown as a tight, polarized monolayer for 7 days on a permeable filter support (0.45 micron pore size) forming the interface between two independent chambers, the upper one bathing the apical (luminal) surface of the epithelial monolayer and the lower one bathing the basolateral (serosal) surface.

Primary, PBMC were obtained and prepared as described in Lagaye et al., (J. Virol, 2001, 75:4780). Then PBMCs were activated with phytohemagglutinin (PHA) for 48 h and inoculated with primary HIV-1 clade C and used at day 7 post infection.

Cervico-vaginal secretions (dilution 1/50) obtained as described in example 2 (weeks 14, 18 and 23, virosome-like vesicles-P1 without adjuvant 36 & 37 i.m., with hRANTES 61 & 63 i.n. or with heat labile toxin 64 &65 i.n.) containing antibodies were incubated at 18° C. for 1 hour with $1.10^6$ HIV-1++PBMC.

To initiate virus transcytosis, $2.10^6$ HIV-1+ PBMC with antibodies were added to the apical chamber. Contact between HIV-1$^+$ PBMC and the epithelial cell monolayer resulted in rapid budding of the HIV-1 virions, followed by their transcytosis from the apical to the basolateral pole of the epithelial cells.

After 2 hours, inhibition of transcytosis by antibody was determined by detection of the protein p24 of HIV in the basolateral medium by ELISA (Coulter, France or PASTEUR SANO.FI, FRANCE). The level of p24 in the absence of vaginal secretion or in presence of a P1 non specific Fab or in the presence of the control IgA 2F5 was measured as negative and positive control respectively. The value of the negative control was taken as 100% of transcytosis and used to express the results.

The experiments were performed at least twice.

Figure 5:
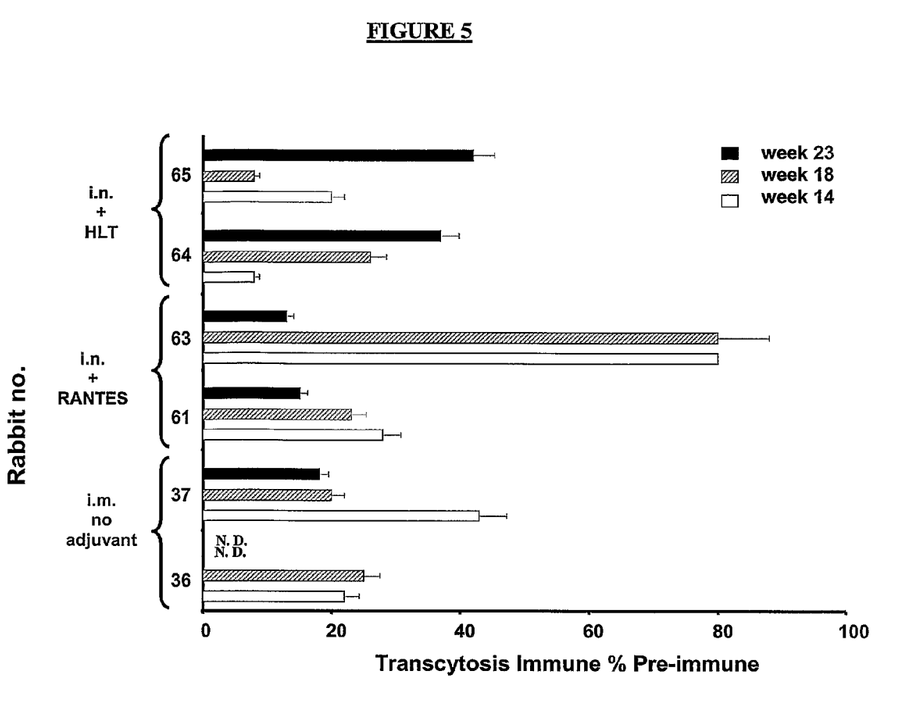
FIG. 5: illustrates the inhibition of HIV-1 transcytosis through HT-29 cells, using PBMC infected with primary viruses and cervico-vaginal secretions (dilution 1/50) obtained as described in example 2 (weeks 14, 18 and 23, virosome-like vesicles-P1 without adjuvant 36 & 37, intra-muscular route, with hRANTES 61 & 63, intra-nasal route or with heat labile toxin 64 & 65, intra-nasal route).

The obtained results shown on FIG. 5.

The results indicated that the cervico-vaginal secretions from rabbits immunized with virosomes-like vesicles-P1 without adjuvant (36 and 37), or with human RANTES (61 and 63), or with the heat labile toxin (HLT) (64 and 65) obtained as described in example 2 were able to restrain the transcytosis HIV-1 of clades C across HT-29 cells.

Without adjuvant and with HLT, an inhibition from 70 to 90% was observed with cervico-vaginal secretion from week 18.

With hRANTES an inhibition from 85 to more than 90% was observed with cervico-vaginal secretion from week 23.

Example 4

Immunization of Macaques with a Vaccine Composition Comprising Virosome-Like Vesicle with Gp-41 Derived Antigen Peptide P1 Located at the External Surface Three groups of 5 to 6 female macaques aged of about 5 years were prepared to receive virosome-like vesicles manufactured as set forth in example 1.

The virosome-like vesicle were either intramuscularly administered (macaques G1.1 to G1.5), or intra-nasally administered (macaques G2.1 to G2.5), or intramuscularly and intra-nasally administered (macaques G3.1 to G3.6).

The following regimen of administration was applied.

Four weeks before the first administration of preparations, macaques received intra-muscular injections of inactivated influenza A (100 µl of inactivated influenza A, 0.01 mg/ml).

Thereafter, macaques received administration of virosome-like vesicles (40 µg, 100 µl) at week 0, 4, 12 and 24.

Rectal lavages and vaginal secretions samples were taken at week 25 and 26.

Level of total antibodies, IgG and IgA were measured according to the following ELISA protocol.

Peptide P1 (100 ng/100 µl/wells, SEQ. ID. NO. 3) in a bicarbonate buffer 50 mM, pH 9.6 was used to coat Nunc plates over night at 4° C.

Plates were saturated with BSA 2%/PBST 0.1% for 1 hour 30/37° C., then washed with PBS-Tween 0.1% buffer.

Samples of rectal washes undiluted or vaginal secretions diluted 1/2 with PBST 0.1% were incubated overnight at 4° C.

Plates were thereafter rinsed with PBS-Tween 0.1% buffer, and incubated with primary antibodies diluted in BSA 2%/PBST 0.1%.

For detection of macaques IgG, an anti-macaque IgG goat antibody (Rockland) (1/15 000) was used followed with an incubation with streptavidine-HRP (Immunotech) diluted 1/50 000.

For the detection of IgA macaques antibody, an anti-macaque IgA goat antibody (Rockland) 1/15 000 was used followed with an incubation with streptavidine-HRP (immunotech) diluted 1/50 000.

A 2F5-IgA monoclonal antibody was used as positive control, followed with an incubation with an anti-human IgA biotin-labelled goat Fab'2, (0.14 µg/ml final) (Caltag H 14015) and revealed with streptavidine-HRP (1/50 000).

A 2F5-IgG monoclonal antibody was used as positive control, followed with an anti-human IgG goat Fab'2 (0.1 µg/ml final) (Rockland 609106123) and revealed with streptavidine-HRP (1/50 000).

The antibodies were incubated for 1 hour at 37° C.

Colorimetric reaction was triggered by addition of the substrate TMB, and stopped by addition of $H_2PO_4$ 1M.

The optical density (OD) was read at 450 nm.

Figure 6:
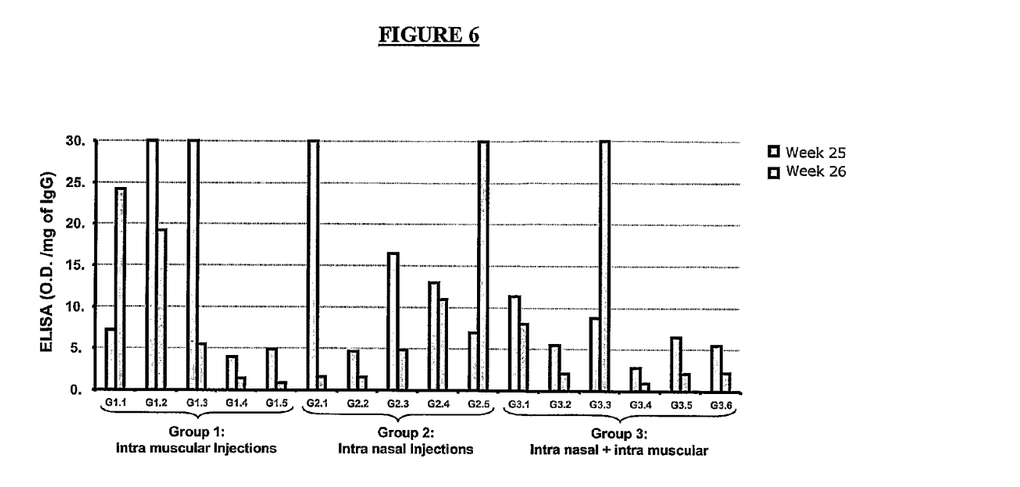
FIG. 6: illustrates dosage by ELISA of IgG in vaginal secretions of female macaques vaccinated with virosome-like vesicles P1 of example 1 at 40 µg/dose at week 0, 4, 12 and 24.
Figure 7:
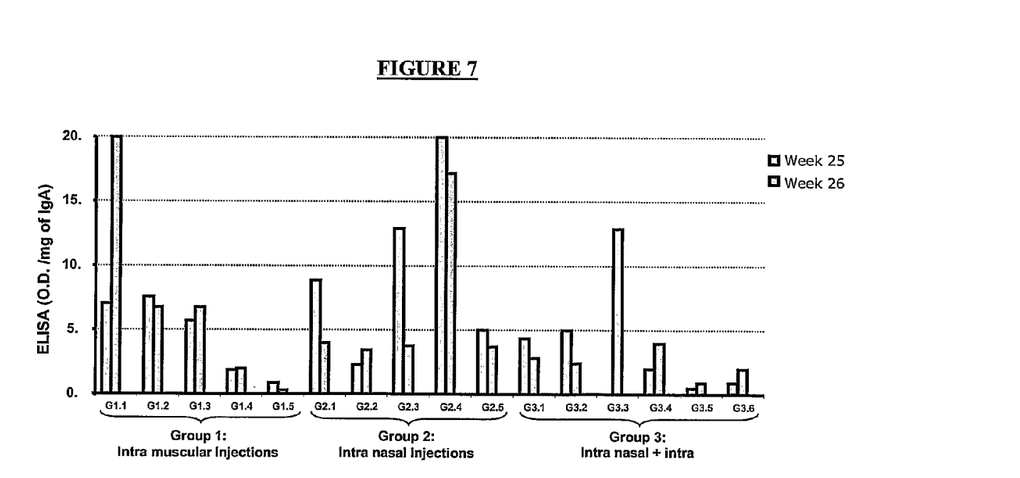
FIG. 7: illustrates dosage by ELISA of IgA in vaginal secretions of female macaques vaccinated with virosome-like vesicles P1 of example 1 at 40 µg/dose at 0, 4, 12 and 24.
Figure 8:
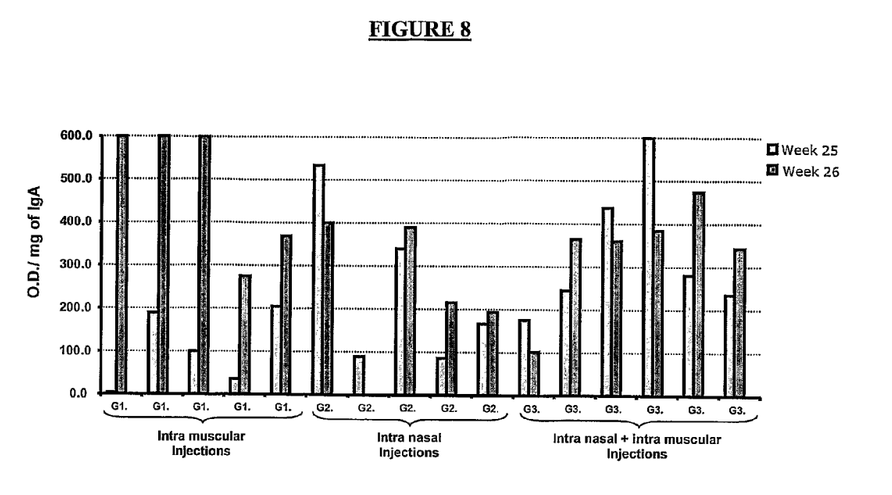
FIG. 8: illustrates dosage by ELISA of IgA in rectal washes of female macaques vaccinated with virosome-like vesicles P1 of example 1 at 40 µg/dose at week 0, 4, 12 and 24.

The obtained results are illustrated on FIGS. 6 and 7 (IgG and IgA vaginal secretions) and FIG. 8 (rectal washes).

Results show that 90 to 95% of female macaques have good levels of levels of specific IgG and IgA antibodies anti-gp41 into their genital secretion, and that more than 95% have specific IgA antibodies anti-gp41 into their rectal washes.

In conclusion, presence of IgG as well as IgA antibodies was observed in vaginal secretions and rectal lavages from immunized females macaques.

The results revealed that an immune response with mucosal antibodies may be obtained with a vaccine of the invention.

Additionally, it is observed that the IgA and IgG antibodies may be redistributed into the genital and intestinal compartments even after vaccination by intramuscular injection in the absence of mucosal adjuvant.

Example 5

Inhibition of HIV Transcytosis with Vaginal Secretions and Rectal Lavages Obtained from Immunized Macaques from Example 4

R5 HIV-1 strains (V29 of primary HIV clade B from NIH and V25 of primary HIV clade C from NIH) transcytosis across epithelial cells and neutralisation of transcytosis by antibodies were performed on epithelial cell line HT-29 grown as a tight, polarized monolayer for 7 days on a permeable filter support (0.45 µm pore size) forming the interface between two independent chambers, the upper one bathing the apical (luminal) surface of the epithelial monolayer and the lower one bathing the basolateral (serosal) surface.

Primary, PBMC were obtained and prepared as described in Lagaye et al., (J. Virol, 2001, 75:4780). Then PBMCs were activated with phytohemagglutinin (PHA) for 48 h and inoculated with primary HIV-1 clade B (V29) or primary HIV-1 clade C (V25) and used at day 7 post infection.

Vaginal secretions (dilution 1/25) or rectal lavages (dilution 1/25) obtained as described in example 4, from week 25 containing antibodies were incubated at 18° C. for 1 hour with $1.10^6$ HIV-1+PBMC.

To initiate virus transcytosis, 2.106 HIV-1+PBMC (V29 or V25) with antibodies were added to the apical chamber. Contact between HIV-1+ PBMC and the epithelial cell monolayer resulted in rapid budding of the HIV-1 virions, followed by their transcytosis from the apical to the basolateral pole of the epithelial cells.

After 2 hours, inhibition of transcytosis by antibody was determined by detection of the protein p24 of HIV in the basolateral medium by ELISA (Coulter, France or PASTEUR SANO.FI, FRANCE). The level of p24 in the absence of vaginal secretion or in presence of a P1 non specific Fab or in the presence of the control IgA 2F5 was measured as negative and positive control respectively. The value of the negative control was taken as 100% of transcytosis and used to express the results.

The experiments were performed at least twice.

Figure 9:
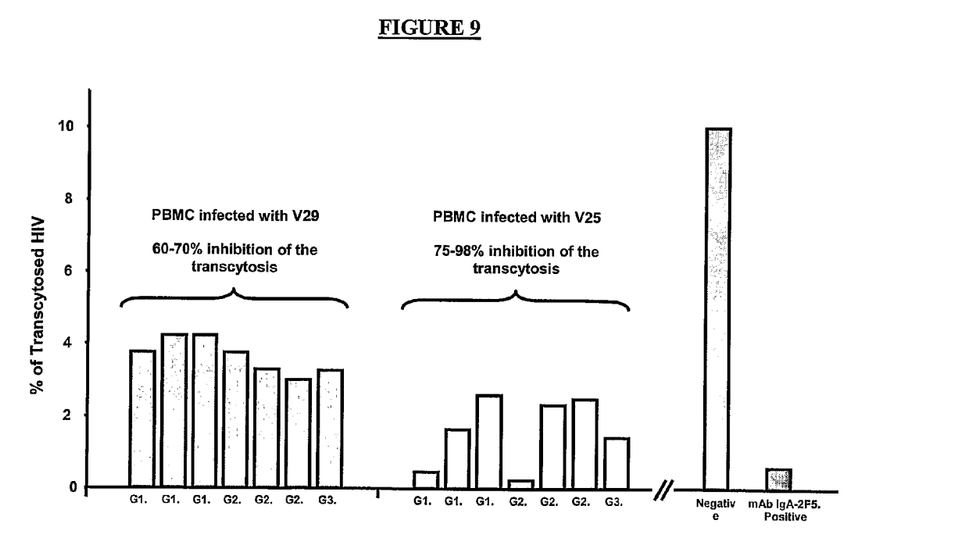
FIG. 9: illustrates the inhibition of R5 HIV strains (V29 primary HIV clade B from the NIH or V25 primary HIV clade C from the NIH) through HT-29 cells using PBMC infected with V29 or V25 with vaginal secretions from week 25 (dilution 1/25) obtained as described in example 4.
Figure 10:
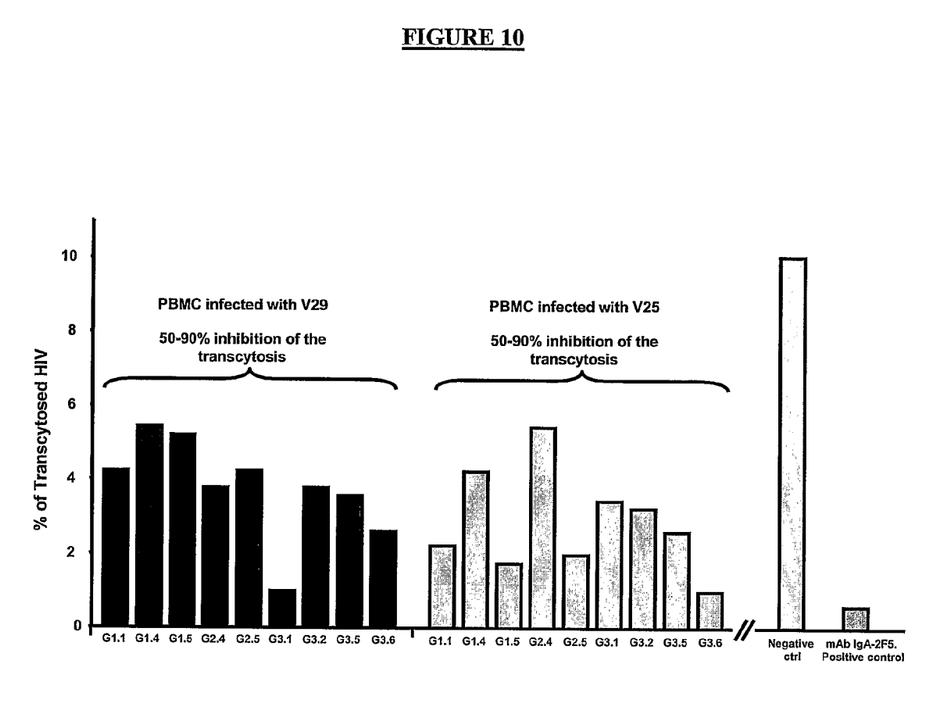
FIG. 10: illustrates the inhibition of R5 HIV strains (V29 primary HIV clade B from the NIH or V25 primary HIV clade C from the NIH) through HT-29 cells using PBMC infected with V29 or V25 with rectal washes from week 25 (dilution 1/25) obtained as described in example 4.

The obtained results shown on FIG. 9 (vaginal secretions) and on FIG. 10 (rectal lavages).

The results indicated that the antibodies were capable of preventing at least 60% of HIV entry across an in vitro human mucosal epithelium model, and up to 98% in two out of sixteen animals.

Therefore, a vaccine of the invention is able to trigger an IgG as well as a mucosal IgA immune response. The mucosal immune response is able to significantly reduce HIV mucosal transcytosis, from different HIV clades.

The invention claimed is:

1. A virosome-like vesicle comprising:
   a gp41-derived antigen attached to a membrane of the virosome-like vesicle, and
   a viral membrane fusion protein, not derived from human immunodeficiency virus (HIV), present in the membrane of the virosome-like vesicle,
   wherein:
   the gp41-derived antigen does not have membrane fusion activity and is configured for conferring on said virosome-like vesicle an ability to induce an immune response against a gp41 protein of HIV; and
   the gp41-derived antigen consists of:
   a P1 peptide having the full length sequence selected from the group consisting of SEQ ID NOs: 2 and 3; and
   an N- or C-terminally positioned cross-linking residue and a spacer sequence consisting of from 2 to 12 spacer residues selected from the group consisting of Gly, Ala, Ser, Asp, Lys, Gln, His, Ile, and Leu residues, the spacer sequence being between and linking the N- or C-terminally positioned cross-linking residue and a corresponding N- or C-terminal gp41-derived antigen terminus.

2. The virosome-like vesicle according to claim 1, wherein said gp41-derived antigen located on the external surface is:
   covalently linked with a lipid of said virosome-like vesicle, or
   intercalated into a lipid bilayer of said virosome-like vesicle by a peptide transmembrane domain not of a wild-type peptide transmembrane domain of a wild-type gp41 protein.

3. The virosome-like vesicle according to claim 2, wherein said covalently linked gp41 derived antigen includes the N- or C-terminally positioned cross-linking residue and the spacer sequence.

4. The virosome-like vesicle according to claim 3, wherein said cross-linking residue is selected from the group consisting Cys and Leu.

5. The virosome-like vesicle according to claim 2, wherein said lipid is selected from the group consisting of amphiphilic PEG derivatives, a phosphatidylethanolamine (PE), a phosphatidylcholine, a phosphatidylserine, a cholesterol, and a mixture thereof.

6. The virosome-like vesicle according to claim 5, wherein said covalently linked gp41 derived antigen is linked to said lipid by a bifunctional succinate linker.

7. The virosome-like vesicle according to claim 2, wherein said gp41 derived antigen is devoid of its peptide transmembrane domain.

8. The virosome-like vesicle according to claim 1, wherein said gp41-derived antigen is anchored to the membrane at or by its C-terminus.

9. The virosome-like vesicle according to claim 1, wherein said gp41 derived antigen is in a form of a mono, a di, a tri, or a tetramer, and mixtures thereof.

10. The virosome-like vesicle according to claim 1, wherein said antigenic gp-41 derived antigen is selected from the group consisting of HIV A, B, C, and D clades.

11. The virosome-like vesicle according to claim 1, wherein said virosome-like vesicle is a fusogenic vesicle comprising a lipid bilayer comprising lipids selected from the group consisting of cationic lipids, synthetic lipids, glycolipids, phospholipids, glycerophospholipids, glycosphingolipids, sphingolipids, cholesterol, and derivatives thereof.

12. The virosome-like vesicle according to claim 1, further comprising at least one adjuvant enhancing and/or mediating an immune response selected from the group consisting of an innate immune response, and an adaptative immune response.

13. The virosome-like vesicle according to claim 12, wherein the adaptative immune response is selected from the group consisting of a $Th_1$ immune response, $Th_2$ immune response, and a mixture thereof.

14. The virosome-like vesicle according to claim 12, wherein said adjuvant is selected from the group consisting of aluminum salts, aluminum phosphate gels, mycobacteria, peptides, keyhole limpet hemocyanin, muramyl dipeptides and tripeptide derivatives, monophosphoryl Lipid A, interleukin-2 (IL-2), IL-12, GM-CSF, ligands from the chemokine family, a lipoprotein of $Gram^+$ bacteria, a yeast cell wall component, a double-stranded RNA, a lipopolysaccharide of $Gram^-$ bacteria, flagellin, a U-rich single-stranded viral RNA, a CpG containing DNA, a Suppressor Of Cytokine Signalling small interfering RNA (SOCS siRNA), mellitin-derived peptides, a panDR epitope (PADRE), and mixtures thereof.

15. The virosome-like vesicle according to claim 12, wherein said adjuvant is a mycobacteria selected from the group consisting of BCG, M. Vaccae, and corynebacterium parvum.

16. The virosome-like vesicle according to claim 12, wherein said adjuvant is a ligand from the chemokine family RANTES (Regulated upon Activation Normal T cell Expressed and Secreted).

17. The virosome-like vesicle according to claim 12, wherein said adjuvant is encapsulated inside said vesicle, and/or incorporated in the lipid bilayer of said vesicle, and/or freely combined with said vesicle.

18. The virosome-like vesicle according to claim 1, further comprising a tissue or cell-specific targeting moiety selected from the group consisting of a cell-surface receptor, a chemokine, a cytokine, a growth-factor, an antibody or an antibody fragment, and a peptide sequence with specificity or specific charge complementary to an adhesion molecule.

19. The virosome-like vesicle according to claim 18, wherein said tissue or cell-specific targeting moiety is incorporated into, or attached to, the lipid bilayer of said vesicle.

20. The virosome-like vesicle according to claim 1, further comprising from one to ten additional antigen(s).

21. The virosome-like vesicle according to claim 20, wherein said additional antigen(s) is(are) selected from the group consisting of HIV peptides derived from structural proteins as encoded by env (gp120, gp41), gag (p9, p17, p24), and pol (p66, p32) genes and from regulatory proteins as encoded by nef, rev, and tat genes, and mixtures thereof, wherein the HIV peptides are devoid of membrane fusion activity.

22. A pharmaceutical composition comprising virosome-like vesicles according to claim 1.

23. The pharmaceutical composition according to claim 22, wherein it comprises vesicles comprising a gp41-derived antigen located on the external surface of said vesicles and vesicles comprising a gp41-derived antigen encapsulated inside said vesicles, as a combined preparation for simultaneous, separate or sequential use in immunotherapy.

24. The pharmaceutical composition according to claim 22, further comprising virosome-like vesicles comprising an antigen not of said gp41-derived antigen as a combined preparation for simultaneous, separate, or sequential use in immunotherapy.

25. A method for the manufacture of a pharmaceutical composition intended to induce an adaptative immune response and/or an innate immune response directed against a gp41 protein of a human imunodeficiency virus comprising adding as an active agent at least one virosome-like vesicle according to claim 1 in a pharmaceutical carrier.

26. A kit for inducing an immune response against a gp41 protein of a human immunodeficiency virus comprising:
   at least a first virosome-like vesicle according to claim 1 comprising at least a first gp41-derived antigen, and
   at least a second virosome-like vesicle according to claim 1 comprising at least a second gp41-derived antigen,
   said first and second gp41-derived antigens being different from each other.

27. The kit according to claim 26, wherein said first gp41-derived antigen is a peptide of amino acids sequence comprising the full length sequence selected from the group consisting of SEQ ID NOs: 2 and 3, and said second gp41-derived antigen is a peptide of amino acids sequence comprising the full length sequence set forth as SEQ ID NO: 1.

28. The virosome-like vesicle according to claim 6, wherein the bifunctional succinate linker is a γ-maleinidobutyric acid N-hydroxysuccinimide ester or a N-γ-maleimidobutyryloxy-succinimide-ester.

29. The virosome-like vesicle of claim 4, wherein the spacer sequence comprises at least a Leu residue.

30. The virosome-like vesicle according to claim 29, wherein the spacer sequence consists of two spacer residues.

* * * * *